United States Patent
Hinkola et al.

(10) Patent No.: US 12,426,837 B2
(45) Date of Patent: Sep. 30, 2025

(54) ANTENNA ARRANGEMENT FOR WRIST-WORN TRAINING COMPUTER

(71) Applicant: Polar Electro Oy, Kempele (FI)

(72) Inventors: Erkki Hinkola, Kempele (FI); Ilkka Heikura, Kempele (FI); Janne Virta, Kempele (FI); Pertti Nissinen, Kempele (FI)

(73) Assignee: Polar Electro Oy, Kempele (FI)

( * ) Notice: Subject to any disclaimer, the term of this patent is extended or adjusted under 35 U.S.C. 154(b) by 405 days.

(21) Appl. No.: 17/739,020

(22) Filed: May 6, 2022

(65) Prior Publication Data

US 2022/0361814 A1 Nov. 17, 2022

(30) Foreign Application Priority Data

May 14, 2021 (EP) .................................... 21173806

(51) Int. Cl.
*A61B 5/00* (2006.01)
*A61B 5/0205* (2006.01)
*A61B 5/024* (2006.01)
*A61B 5/053* (2021.01)
*A61B 5/11* (2006.01)
(Continued)

(52) U.S. Cl.
CPC ............ *A61B 5/681* (2013.01); *A61B 5/0002* (2013.01); *A61B 5/02055* (2013.01); *A61B 5/02416* (2013.01); *A61B 5/02438* (2013.01); *A61B 5/053* (2013.01); *A61B 5/1112* (2013.01);
(Continued)

(58) Field of Classification Search
CPC ............ A61B 5/0002; A61B 5/02055; A61B 5/02416; A61B 5/02438; A61B 5/053; A61B 5/1112; A61B 5/14542; A61B 5/318; A61B 5/4869; A61B 5/681; G06F 1/163; H01Q 1/273; H01Q 5/378; H01Q 7/00

See application file for complete search history.

(56) References Cited

U.S. PATENT DOCUMENTS

2002/0124392 A1* 9/2002 Chung ............ G06K 19/07745
257/E23.07
2010/0328162 A1* 12/2010 Matsushita ............ H01Q 9/27
343/700 MS
(Continued)

FOREIGN PATENT DOCUMENTS

| CN | 111916887 A | 11/2020 |
| JP | 2019-153979 A | 9/2019 |
| WO | 2021/071667 A1 | 4/2021 |

OTHER PUBLICATIONS

Extended European Search Report received for EP Patent Application Serial No. 21173806.7 dated Oct. 21, 2021, 9 pages.

*Primary Examiner* — Benjamin J Klein
*Assistant Examiner* — Vynn V Huh
(74) *Attorney, Agent, or Firm* — FisherBroyles, LLP (57) ABSTRACT

A wrist-worn training computer includes one or more biosensors; a casing; a display lens positioned against the casing to form an interface between the display lens and the casing, and to enclose together with the casing an enclosed space between the casing and the display lens; a first part of an antenna of a satellite navigation receiver disposed within the enclosed space; and a gasket positioned along the interface between the display lens and the casing to seal the enclosed space. The gasket comprises electrically conductive material that forms a second part of the antenna.

10 Claims, 7 Drawing Sheets

Section A-A (51) Int. Cl.
　　　*A61B 5/145*　　　(2006.01)
　　　*A61B 5/318*　　　(2021.01)
　　　*G06F 1/16*　　　(2006.01)
　　　*H01Q 1/27*　　　(2006.01)
　　　*H01Q 5/378*　　　(2015.01)
　　　*H01Q 7/00*　　　(2006.01)

(52) U.S. Cl.
　　　CPC .......... *A61B 5/14542* (2013.01); *A61B 5/318* (2021.01); *A61B 5/4869* (2013.01); *G06F 1/163* (2013.01)

(56) References Cited

U.S. PATENT DOCUMENTS

| | | | |
|---|---|---|---|
| 2011/0241948 A1* | 10/2011 | Bevelacqua | H01Q 13/18 343/702 |
| 2014/0225786 A1* | 8/2014 | Lyons | H01Q 9/40 343/702 |
| 2014/0266787 A1* | 9/2014 | Tran | A61B 5/0205 340/870.07 |
| 2016/0036120 A1* | 2/2016 | Sepänniitty | H01Q 1/243 343/702 |
| 2016/0054711 A1 | 2/2016 | Fujisawa | |
| 2017/0090521 A1* | 3/2017 | de Jong | G06F 1/1656 |
| 2019/0051975 A1 | 2/2019 | Hasei et al. | |
| 2020/0243952 A1 | 7/2020 | Zhu et al. | |

\* cited by examiner

ANTENNA ARRANGEMENT FOR WRIST-WORN TRAINING COMPUTER

CROSS-REFERENCE TO RELATED APPLICATION

This application claims benefit and priority to European Application No. 21173806.7, filed May 14, 2021, which is incorporated by reference herein in its entirety.

BACKGROUND

Field

Various embodiments relate to antenna arrangements in a wrist-worn training computer.

SUMMARY

Wrist devices, such as wrist-worn training computers, may be equipped with a large number of features, such as various sensors used to measure physiological parameters, features for wireless communication, and global or local positioning features. Especially antenna arrangements may be large and add to the weight of the wrist device. A training computer with good performance may be large and heavy due to the different components required for each feature. Such a device may be uncomfortable to wear. Wrist devices may also be exposed to harsh conditions, especially outdoors. Additional components intended for protecting the device are often included in such devices, further increasing their size and weight. Solutions that provide good performance while allowing a reasonable size and weight are therefore desirable.

According to an aspect, there is provided subject matter of independent claims. Dependent claims define some embodiments.

One or more examples of implementations are set forth in more detail in the accompanying drawings and the description of embodiments.

LIST OF DRAWINGS

Some embodiments will now be described with reference to the accompanying drawings, in which

FIGS. 4-6C illustrate relative positions of a display lens, a gasket, and a casing of a wrist-worn training computer;

DETAILED DESCRIPTION

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Reference numbers, both in the description of the embodiments and in the claims, serve to illustrate the embodiments with reference to the drawings, without limiting it to these examples only.

The embodiments and features, if any, disclosed in the following description that do not fall under the scope of the independent claims are to be interpreted as examples useful for understanding various embodiments of the invention.

The present invention is concerned with a wrist device, specifically a wrist-worn training computer, comprising one or more biosensors; a casing; a display lens positioned against the casing to form an interface between the display lens and the casing, and to enclose together with the casing an enclosed space between the casing and the display lens; a first part of an antenna of a satellite navigation receiver disposed within the enclosed space; a gasket positioned along the interface between the display lens and the casing to seal the enclosed space, wherein the gasket comprises electrically conductive material that forms a second part of the antenna.

The terms 'wrist device' and 'wrist-worn training computer' are used interchangeably herein. The wrist device has an antenna of a satellite navigation receiver. The antenna may be configured to receive global navigation satellite system (GNSS) signals. The antenna may thus be used to communicate with GNSS satellites and to carry out positioning, navigation, and tracking of the location of the wrist device. The ability and performance of the wrist device in carrying out the aforementioned tasks is dependent on the radiation characteristics of the satellite navigation receiver antenna. Especially the right hand circularly polarized (RHCP) gain of the antenna is important when receiving RHCP signals from navigation satellites. The attenuation of reflected signals or poor left hand circularly polarized (LHCP) gain of the antenna is also important.

The satellite navigation receiver antenna has two parts, of which the first part is disposed within the enclosed space, integrated within the wrist device. When measured alone, the first part of the antenna has a moderate maximum RHCP gain, particularly when the casing is plastics of other electrically non-conductive material.

The wrist device further comprises a gasket positioned along the interface between the display lens and the casing. The gasket serves two purposes: the first purpose of the gasket is to seal the interface between the display lens and the casing, therefore also sealing the enclosed space between the display lens and the casing. The second purpose of the gasket is to operate as the second part of the satellite navigation receiver antenna, further improving its radiation characteristics. The second purpose is achieved by electrically conductive material comprised within the gasket. The electrically conductive material forming the second part of the antenna coupled with the first part of the antenna form the satellite navigation receiver antenna. The antenna has improved radiation characteristics and RHCP gain when compared to the first part of the antenna alone. In particular with the plastic casing, the improved radiation characteristics can be gained without increasing the size or dimensions of the first part of the antenna inside the casing.

Even though the radiation characteristics of the antenna have been discussed mainly with respect to improving RHCP gain, the invention may also be applied to improve other radiation characteristics of the antenna, such as LHCP gain, for example. However, the embodiments described herein are focused on improving RHCP gain and reducing LHCP gain to achieve improved reception of RHCP navigation signals from navigation satellites.

The casing or chassis may provide a frame or a body of the wrist device. The casing may be used to protect internal components of the wrist device by shielding them from external factors, such as moisture or spillage. The casing may be made of an electrically insulating material. In an embodiment, the casing is a plastic casing, which also has the advantage of being light-weight.

The display lens is positioned against the casing, forming an interface between the display lens and the casing. The display lens has an external surface facing away from the casing, and an internal surface facing towards the casing. The display lens and the casing further enclose together an enclosed space between the casing and the display lens. The display lens may also be used to protect internal components of the wrist device. The display lens may be made of transparent material such as glass or a transparent plastics material.

The enclosed space between the display lens and the casing is sealed with the gasket to protect sensitive electronic and non-electronic components disposed therein. Humidity, moisture, fluid spills as well as dust and other particles may damage the sensitive components and potentially render the device unusable. A wrist device used for sports may also be submerged during certain activities, such as swimming. A waterproof seal to protect the sensitive components may therefore be required and is achieved by the gasket.

The conductive material comprised in the gasket may not compromise its ability to seal the interface between the display lens and the casing, but instead allows for the gasket to serve another purpose in forming the second part of the antenna.

The wrist device may be considered a smart watch or a sports watch. The wrist device may be capable of measuring and/or monitoring physical and/or physiological parameters, such as a temperature or a heart rate of the wearer of the wrist device. The biosensors may be configured to sense motion, acceleration, temperature, electrocardiogram (ECG), photoplethysmogram (PPG), or electrical impedance, for example. These capabilities may be achieved by a variety of biosensors. In an embodiment, the biosensors comprise at least one of: an optical heart rate sensor, an oxygen saturation sensor, a temperature sensor, an electrocardiography sensor, a bioimpedance sensor, a body composition sensor.

The wrist device may also have wireless communication capabilities, such as Bluetooth, cellular, near field communication (NFC), and ultra-wideband (UWB) communication capabilities.

Figure 1:
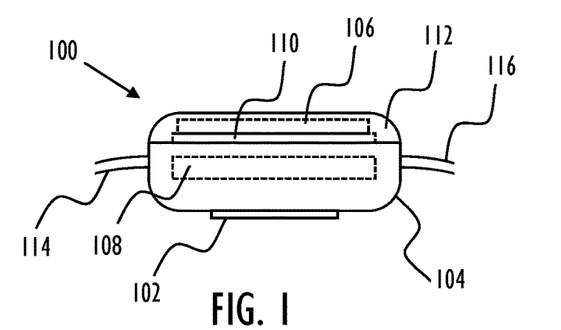
FIGS. 1-3 illustrate embodiments of a wrist-worn training computer.

A side view of an embodiment of the wrist device is shown in FIG. 1. The wrist device 100 comprises the casing 104 and the display lens 106, and the interface between the casing and the display lens is sealed by the gasket 110. The gasket is positioned against the internal surface of the display lens. The first part of the antenna 108 is enclosed in the space between the display lens and the casing. Biosensors 102 such as an optical heart rate sensor are also illustrated on the wrist-facing surface of the wrist device. Straps 114, 116 of a wristband for attaching the watch to the wrist of its user may extend from opposite sides of the casing.

A bezel 112 is also included in the embodiment of FIG. 1. The bezel may be made of the same material as the casing, or it may be made of a different material. The bezel may be made of an electrically conductive material or an electrically non-conductive material. In the case of an electrically conductive bezel, the bezel may form a third part of the antenna. The bezel may be an integral part of the casing, or it may be a separate part attached to the rest of the casing. The bezel may surround the display lens, and it may extend past the external surface of the display lens, so that the display lens may appear sunken, as illustrated in FIG. 1. The bezel may also extend over the display lens to cover a part of the external surface of the display lens. The bezel may be used to secure the display lens in its place against the casing. The interface between the display lens and the casing may be between the display lens and the bezel, or between the display lens and both the bezel and another part of the casing.

Figure 2:
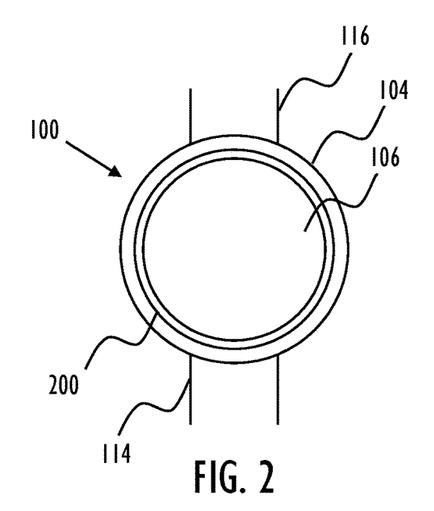

FIG. 2 illustrates another embodiment of the wrist device 100. The display lens 106 of the embodiment has a round shape, however, other shapes such as a rectangular shape or a square shape are also possible. A gasket 200 may be fitted around the display lens, against the edge of the display lens, and it may have an annular shape to match the shape of the round edge of the display lens. The gasket may be dimensioned to match the size of the display lens to ensure a tight seal against the edge of the display lens. The first part of the antenna enclosed between the display lens and the casing is not shown.

Figure 3:
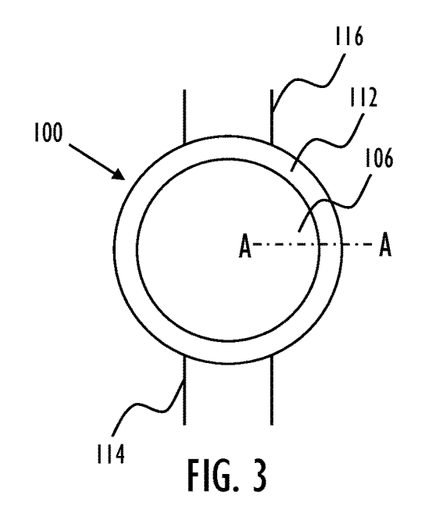
Figure 4:
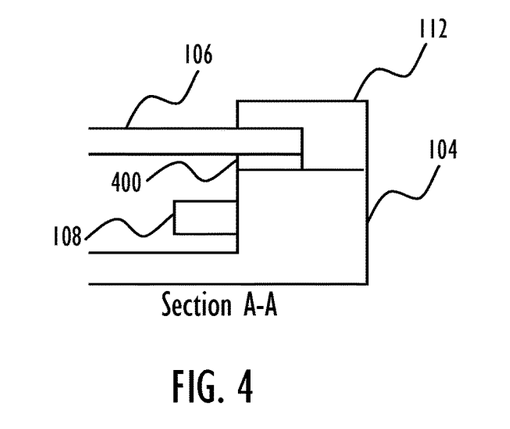
Figure 5:
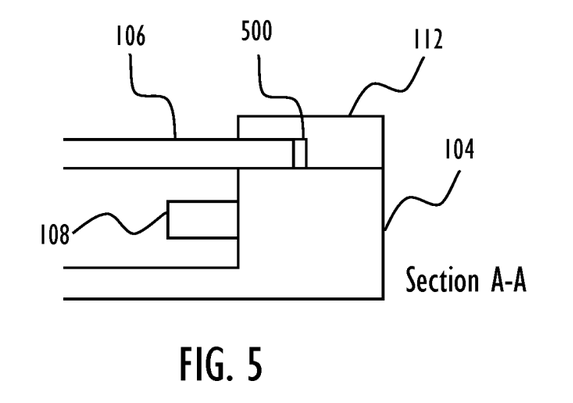
Figure 6A:
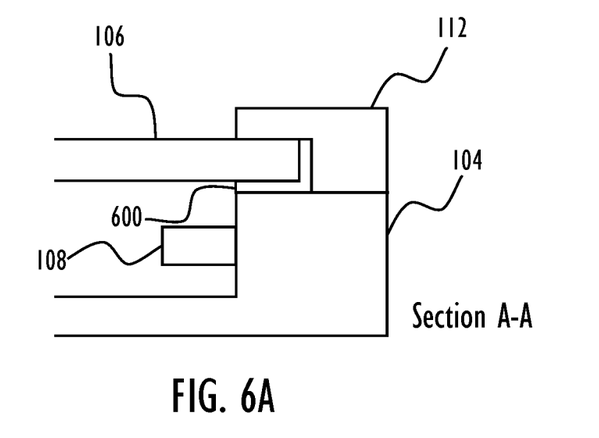
Figure 6B:
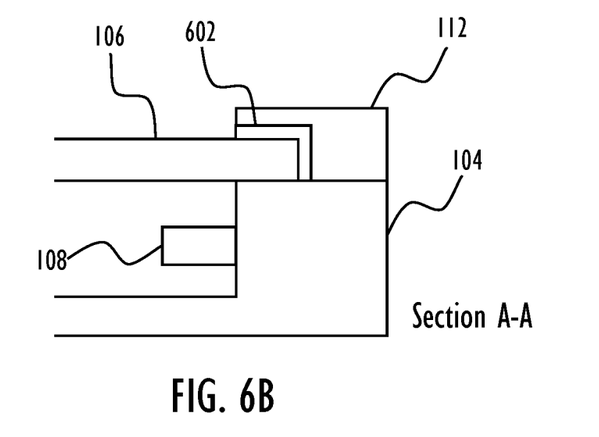
Figure 6C:
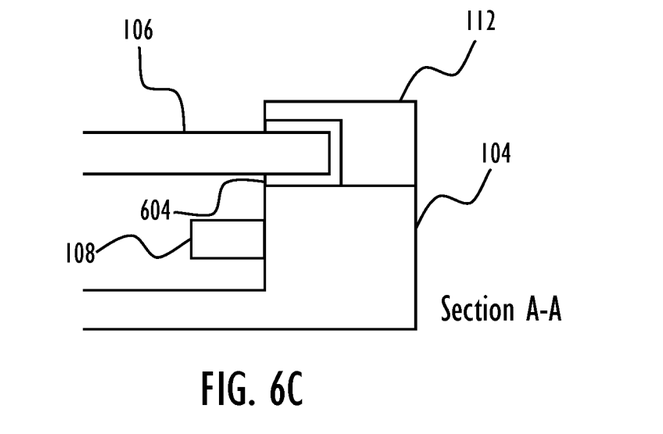

FIG. 3 illustrates an embodiment with a similar appearance to that of FIG. 2, with the addition of a bezel 112. The sealing gasket may be entirely or partially concealed by the display lens, the casing and/or the bezel, and is not visible in FIG. 3. Embodiments with different configurations and relative positions of the gasket, the display lens, and the bezel are illustrated in FIGS. 4-6. Each one of these figures represents an alternative embodiment of the gasket, the display lens, and the bezel, that may correspond to the cross-section A-A of the wrist device illustrated in FIG. 3. The different configurations are discussed in further detail below.

The embodiment of FIG. 4 comprises a bezel 112 that extends over the external surface of the display lens. The bezel is shown to be touching the external surface of the display lens, however, it is not necessary for the bezel to be in contact with the external surface of the display lens, and a gap between the two is allowed. However, if the bezel is touching or in contact with the display lens, it may be used to secure the display lens in its place. Moreover, dirt build-up may occur in a gap between the bezel and the display lens. The gasket 400 is positioned between the internal surface of the display lens and the casing. The gasket may also extend further along the casing past the edge of the display lens, between the bezel and the casing. In an embodiment wherein the bezel is separate from the casing, the gasket may extend between the bezel and the casing and seal an interface between the bezel and the casing. The gasket may also extend further into the enclosed space. The first part of the antenna 108 is disposed in the enclosed space between the casing and the display lens, and adjacent to an inner wall of the casing. The first part of the antenna may be attached to the inner wall of the casing, and it may be at least partially embedded to the inner wall of the casing.

FIG. 5 illustrates an embodiment wherein the gasket 500 is arranged against the edge of the display lens, in a similar manner as in the embodiment of FIG. 2. The embodiment also includes a bezel 112 extending over the external surface of the display lens. The gasket 500 is between the edge of the display lens and the bezel of the casing. The gasket is also surrounded by the casing and the bezel on its top and bottom sides, as shown in FIG. 5.

In an embodiment, the gasket has an L-shaped cross-section. As illustrated in FIG. 6A, the gasket 600 may be against both the internal surface and the edge of the display lens. In FIG. 6, the gasket is also against both the casing and the bezel of the wrist device. In an alternative embodiment illustrated in FIG. 6B, the gasket 602 with an L-shaped cross-section may be against both the external surface and the edge of the display lens. In a yet alternative embodiment illustrated in FIG. 6C, the gasket 604 has a U-shaped cross-section, allowing for it to be against the display lens along the edge, the internal surface, and the external surface of the display lens.

Different shapes of the first part of the antenna, the second part of the antenna, i.e. the gasket, and their relative positions may affect the radiation characteristics of the antenna. Some possible shapes of the gasket and its position relative to other parts of the wrist device have been described above, and more embodiments are discussed in detail below.

In an embodiment, the first part of the antenna and the second part of the antenna are capacitively coupled. Capacitive coupling may be achieved by the proximity of the first part and the second part of the antenna. The first part of the antenna and the second part of the antenna may be separated by a distance of 2-3 millimetres (mm), or by a distance smaller than 2 mm, for example. Close proximity, i.e. a small distance between the first part of the antenna and the second part of the antenna also allows for a smaller size of the wrist device.

In an embodiment, the electrically conductive material forms a closed loop. The gasket itself may also form a closed loop along the interface between the display lens and the casing to seal the interface effectively. In a similar manner, the electrically conductive material may extend along the gasket to form a closed loop. The closed loop formed by the electrically conductive material forming the second part of the antenna may improve the radiation characteristics of the antenna.

In an embodiment, the electrically conductive material forms an annular loop. The gasket itself may also have an annular shape, such as in the embodiment of FIG. 2. The annular loop may also improve the radiation characteristics of the antenna.

In an embodiment, the electrically conductive material forms a penannular shape. The electrically conductive material may form an almost complete annulus with a break. In another embodiment, the electrically conductive material forms a semi-annular shape. In both embodiments, the shape of the conductive material may improve the radiation characteristics of the antenna.

In an embodiment, the electrically conductive material extends in a first plane parallel to the display lens and turns to a second plane perpendicular to the display lens. The conductive material may extend in the first plane along the internal surface of the display lens, or around the display lens along the edge of the display lens, for example. The conductive material may also extend in the second plane perpendicular to the display lens, such as transversely along the edge of the display lens, such as from the level of the internal surface to the level of the external surface of the display lens. An example of this embodiment is the L-shaped gasket 600 of FIG. 6.

The gasket may also serve a third purpose in addition to sealing interface between the display lens and the casing and forming the second part of the antenna.

In an embodiment, the gasket comprises a plurality of layers comprising an adhesive layer and an electrically conductive layer made of the electrically conductive material that forms the second part of the antenna. In other words, the gasket has a multi-layered structure. Some layers of the multi-layered structure may be similar, or all layers of the multi-layered structure may be different. Layers with different properties may perform different functions of the gasket.

The adhesive layer may be used to attach the gasket to the display lens and/or the casing, and/or to attach the display lens to the casing. Other means for attaching the display lens to the casing, such as snap-fit joints, may also be used. The display lens may also be attached to a bezel of the casing, and it may be secured between the bezel and the casing, as illustrated in FIGS. 4-6. The adhesive layer may join the gasket to the display lens and/or the casing, and the adhesive layer may prevent movement of the joined parts relative to each other, ensuring that the gasket is not displaced, and the seal is not compromised.

The electrically conductive material forming the second part of the antenna may be located within a layer of the multi-layered gasket. The conductive layer may be very thin and have a thickness of less than 0.1 millimetres (mm), e.g. 0.05 mm. The electrically conductive material may be copper or aluminium, for example. Correspondingly, the conductive layer may be made of metal foil, such as copper or aluminium foil. In another embodiment, the gasket comprises two or more electrically conductive layers made of the electrically conductive material, that together form the second part of the antenna.

The multi-layered gasket may also comprise other, different kinds of layers in addition to the electrically conductive layer(s). In an embodiment, the gasket comprises a first adhesive layer and a second adhesive layer, wherein the conductive layer is between the first adhesive layer and the second adhesive layer. The first adhesive layer and the second adhesive layer may be made of electrically insulating materials to electrically insulate the conductive layer that is sandwiched between the adhesive layers. The first and second adhesive layers may be made of adhesive tape. The adhesive tape may be two-sided, i.e. having an adhesive surface on both sides of the tape. The first adhesive layer made of two-sided adhesive tape may adhere to a first side of the electrically conductive material, such as thin metal foil, and the second adhesive layer made of two-sided adhesive tape may adhere to a second side of the electrically conductive material, leaving the other side of both adhesive tapes exposed for further attachment. The resulting multi-layered gasket may still be very thin, with a thickness of 0.45 mm, for example.

Figure 7:
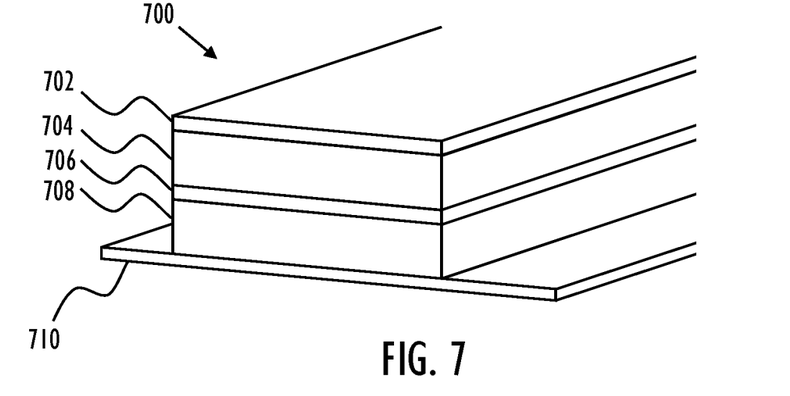
FIG. 7 illustrates a multi-layered gasket structure.

A multi-layered gasket structure 700 with a plurality of layers is illustrated in FIG. 7. In addition to the electrically conductive layer 706 in between a first adhesive layer 704 and a second adhesive layer 708, the structure includes a liner 702 and a carrier 710. The liner and the carrier cover the otherwise exposed adhesive surfaces of the first and second adhesive layers. The liner is also used to align the gasket during assembly of the wrist device. The liner and the carrier are removed from the gasket during the assembly of the wrist device.

In an embodiment, the gasket is positioned so that the first adhesive layer is against the display lens to adhere the gasket to the display lens, and the second adhesive layer is against the casing to adhere the gasket to the casing, so that the display lens adheres to the casing via the gasket. To achieve the aforementioned positioning, the carrier layer of the gasket may be removed, exposing the adhesive surface on the second adhesive layer. The exposed adhesive surface on the second adhesive layer of the gasket may be placed against the casing, and the adhesive of the second adhesive layer attaches the gasket to the casing. The liner layer of the gasket may then be removed, exposing the adhesive surface on the first adhesive layer. The display lens may be placed against the first adhesive layer, and the adhesive of the first adhesive layer attaches the gasket to the display lens. The display lens is therefore attached to the casing via the gasket.

As an alternative to the multi-layered structure, the gasket may also have a uniform structure. In an embodiment, the gasket has a uniform structure made of the electrically conductive material. The uniform structure may be moulded to any desired shape of the gasket, including the annular shape described earlier.

In an embodiment, the electrically conductive material is an electrically conductive paste having electrically conductive particles dispersed in a medium. Electrical conductivity of the paste is achieved by the conductive particles. The conductive particles may be copper, silver, or nickel particles, for example. The paste may be applied to the interface between the display lens and the casing during the assembly of the wrist device.

In an embodiment, the electrically conductive paste is an electrically conductive adhesive that adheres the display lens to the casing. The paste may comprise an adhesive component, such as a silicone or epoxy adhesive, and the conductive particles are dispersed within the adhesive component. Like with the multi-layered gasket with adhesive layers, the gasket made of the electrically conductive adhesive may be used to attach the casing to the display lens. The conductive adhesive may be applied to the casing and/or the display lens, and the casing and the display lens are placed against each other. The conductive adhesive forms a seal and joins the casing and the display lens together. The conductive adhesive may also be applied to the bezel of the casing to join the bezel to the display lens and/or the casing.

Figure 8:
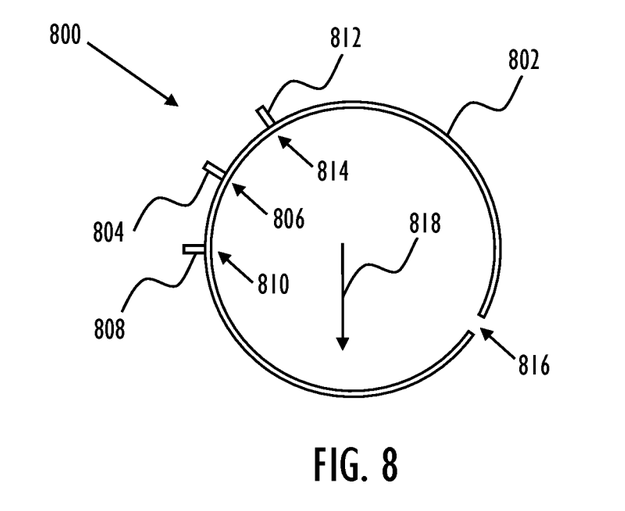
FIG. 8 illustrates an embodiment of a folded dipole antenna.

According to another aspect of the invention, the first part of the antenna is a folded dipole type of antenna with a gamma match, or a gamma matched dipole antenna with or without ground point impedance tuning, referred to as 'folded dipole antenna' herein. An embodiment of the folded dipole antenna is illustrated in FIG. 8. The folded dipole antenna 800 comprises: an elongated conductive element 802; a feed contact 804 coupled to the conductive element at a feed point 806; a first ground contact 808 coupled to the conductive element at a first ground point 810; and a second ground contact 812 coupled to the conductive element at a second ground point 814.

The radiation characteristics of the folded dipole antenna may depend on the locations of the feed point, the first ground point and the second ground point, and the distance between the ends of the folded dipole antenna. The radiation characteristics may also depend on electrical components used to couple the ground contacts to a ground plane. A desired radiation pattern and polarization of the folded dipole antenna may thus be achieved by adjusting these factors. The folded dipole antenna may be configured to one or more desired frequency bands, such as: GPS L5 at 1176.45 MHz; GNSS L1 bands including Galileo, BeiDou, GLONASS, GPS, at frequencies of 1561-1609 MHz; and Bluetooth at frequencies of 2400-2483.5 MHz.

In an embodiment, the feed point is between the first ground point and the second ground point and at certain distances from the ground points, respectively. The feed point may be positioned in a location along the conductive element that is between the locations of the first and second ground point. Alternatively, the first ground point may be between the feed point and the second ground point, or the second ground point may be between the feed point and the first ground point. Radiation characteristics of the folded dipole antenna may be modified by positioning of the feed point.

In an embodiment, the feed point is at a midpoint of the conductive element. In other words, the feed point is at an equal distance from both ends of the conductive element. The conductive element may be symmetrical about the feed point. The location of the feed point at the midpoint of the conductive element may also improve the radiation characteristics of the folded dipole antenna. In another embodiment, the feed point is substantially in a midpoint between the ground points 810, 814. In yet another embodiment, the first ground point is at a midpoint of the conductive element, i.e., at an equal distance from both ends of the conductive element.

In an embodiment, the feed point is the only feed point of the folded dipole antenna. Only one feed point allows for a simpler design of the folded dipole antenna and it may also affect its radiation characteristics.

There are some options for the selection of components used to couple the ground contacts to the ground plane. The types and values of the components may affect the polarization and the radiation pattern of the folded dipole antenna. In an embodiment, the folded dipole antenna comprises a first capacitor to couple the first ground contact to the ground plane, and a second capacitor to couple the second ground contact to the ground plane. The capacitors may have the same values, or they may have different values. The values of the capacitors may be in a range of 0.1 to 2.0 picofarads (pF), for example. In an embodiment, the first capacitor has a value of 0.6 pF, and the second capacitor has a value of 0.3 pF. In another embodiment, the first capacitor has a value of 1.4 pF, and the second capacitor has a value of 0.9 pF.

The components used to couple the ground contacts to the ground plane may also include inductors, conductors, diodes, and/or resistors. In an embodiment, the folded dipole antenna comprises a first inductor to couple the first ground contact to the ground plane, and a second inductor to couple the second ground contact to the ground plane. The inductors may have the same values, or they may have different values, and their values may affect the radiation characteristics of the folded dipole antenna. In an embodiment, the folded dipole antenna comprises at least one of: an inductor and a capacitor, to couple the first ground contact or the second ground contact to the ground plane. In a related embodiment, the folded dipole antenna further comprises a conductor to couple the first ground contact or the second ground contact to the ground plane. In another embodiment, the folded dipole antenna comprises an inductor and a capacitor to couple the first and second ground contact to the ground plane. In yet another embodiment, the folded dipole antenna comprises a diode, specifically an electrostatic discharge (ESD) diode, to couple the first or the second ground contact to the ground plane.

In an embodiment, the folded dipole antenna comprises an impedance matching circuit coupled to the feed contact.

Impedance matching may be done to maximize power transfer and/or minimize signal reflection.

At a first frequency, a first loop may be formed along the folded dipole antenna via the feed contact and the grounded first ground contact. At a second frequency, a second loop may be formed along the folded dipole antenna via the feed contact and the grounded second ground contact.

The shape of the conductive element of the folded dipole antenna may also have an effect on its radiation characteristics. In an embodiment, the conductive element forms a penannular shape with a break 816 between the ends of the conductive element, as illustrated in FIG. 8. A penannular shape may be conveniently fitted to a wrist device, as the conductive element may extend along a wall of a cylindrical watch casing, specifically along the inner wall of the casing. The break may have a width of 1-4 mm, i.e. the ends of the conductive element may be separated by a distance of 1-4 mm, for example.

In an embodiment wherein the conductive element has a penannular shape as described above, the feed point is located opposite the break between the ends of the conductive element, the first ground point is located $1/12^{th}$ of a full revolution anticlockwise from the feed point, and the second ground point is located $1/12^{th}$ of a full revolution clockwise from the feed point. FIG. 8 also approximately shows the above positions of the feed point, the first and second ground points, and the break.

The folded dipole antenna according to the above embodiment may be configured to receive RHCP signals from navigational satellites. The radiation pattern of the above folded dipole antenna may be focused in directions between a direction 818 pointing $1/6^{th}$ of a full revolution clockwise of the break 816, and a perpendicular direction towards the viewer of FIG. 8.

The folded dipole antenna may be positioned in the wrist device in a way that allows for directing the RHCP radiation pattern towards navigational satellites when the wrist device is worn on the wrist of its user. The positioning and orientation of the folded dipole antenna is now discussed with reference to an imaginary clock face of the wrist device.

Wrist devices, such as wristwatches, are often worn so that a display or a clock face of a wrist device is on the back side of the wrist, and the straps of the wristband extend across the palm side of the wrist. The clock face of an analog wristwatch is traditionally oriented so that when the wristwatch is worn on the left hand, the direction of 3 o'clock points towards the fingers, the direction of 6 o'clock is on the radial side of the wrist, the direction of 9 o'clock points towards the elbow, and the direction of 12 o'clock is on the ulnar side of the wrist. When worn on the right hand, the direction of 3 o'clock points towards the elbow, the direction of 6 o'clock is on the radial side of the wrist, the direction of 9 o'clock points towards the fingers, and the direction of 12 o'clock is on the ulnar side of the wrist.

Figure 9:
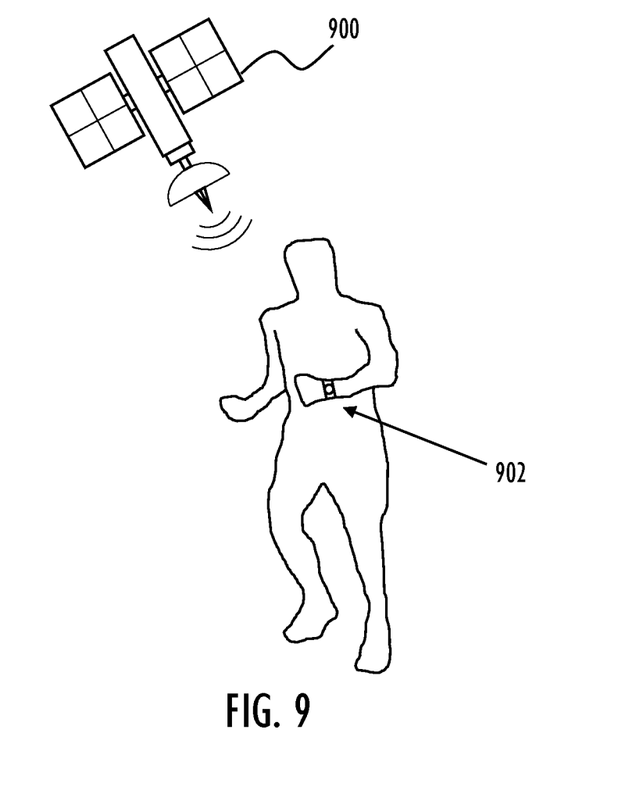
FIG. 9 illustrates a user wearing a wrist device.

When the user of a wrist device 902 is exercising, such as running or walking, their arms are often bent at the elbow so that the radial side of the wrist is pointing upwards or towards the sky, as shown in FIG. 9. As discussed above, the direction of 6 o'clock of a clock face of a wrist device is usually on the radial side of the wrist, irrespective of whether the wrist device is worn on the left hand or the right hand. The direction of 6 o'clock is therefore pointing towards the sky, and towards navigational satellites 900. During other activities, such as cycling, the back side of the wrist may also be facing towards the sky. As the display of the wrist device is often on the back side of the wrist, the display may therefore also be pointing towards the sky, and towards navigational satellites.

Figure 10:
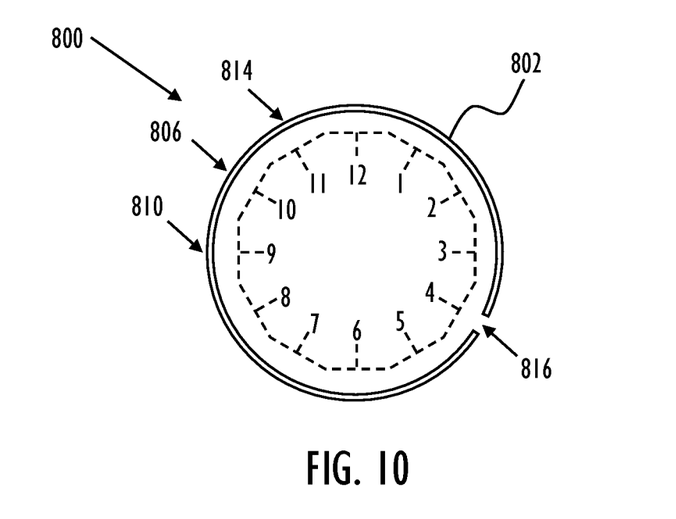
FIG. 10 illustrates a folded dipole antenna and an imaginary clock face.

In an embodiment of the wrist device, the folded dipole antenna is positioned relative to an imaginary clock face of the wrist device so that the break between the open ends of the antenna is in a direction of 4 o'clock, the first ground point is in the direction of 9 o'clock, the feed point is in a direction of 10 o'clock, and the second ground point is in a direction of 11 o'clock. The positioning of the folded dipole antenna with respect to an imaginary clock face is illustrated in FIG. 10.

The above positioning allows for directing the radiation pattern of the folded dipole antenna towards navigational satellites in the sky. The radiation pattern of the folded dipole antenna that was described earlier may now be described in relation to the wrist device: the radiation pattern may be focused in directions between the direction of 6 o'clock on the imaginary clock face of the wrist device, and a perpendicular direction away from the imaginary clock face, which corresponds to a perpendicular direction away from the display lens or screen of the wrist device.

As was mentioned, the clock face discussed above is an imaginary analog clock face. The wrist device may have a clock face similar to the imaginary clock face, or the wrist device may have a digital clock face as shown in FIG. 11, or the wrist device may not have a clock face at all.

Figure 11:
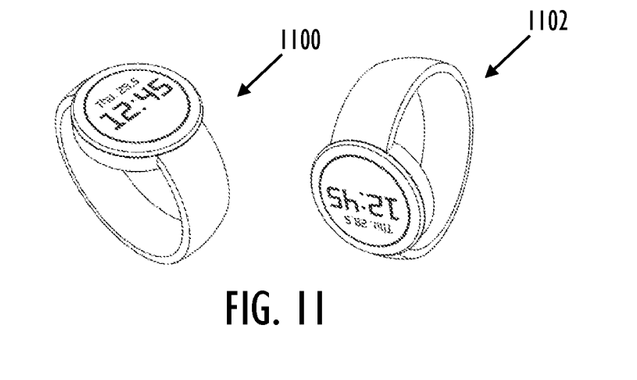
FIG. 11 illustrates embodiments of a wrist-worn training computer in different orientations.

FIG. 11 illustrates a wrist device 1100 in an orientation that may occur during an activity such as cycling, where the display is facing up towards the sky. A wrist device 1102 is also illustrated in an orientation that may occur while running or walking. The bottom of the digital clock face of wrist device 1102, corresponding to the direction of 6 o'clock in the imaginary analog clock face, is pointing towards the navigational satellite 900. Navigational signals from the satellite 900 are received from the direction of 6 o'clock of the imaginary clock face. The display of wrist device 1100 is pointing towards the navigational satellite 900, meaning that navigational signals from the satellite are received in a perpendicular direction away from the display screen. Both devices 1100 and 1102 are oriented in a way that directs the RHCP radiation pattern towards the navigational satellite 900.

Figure 12:
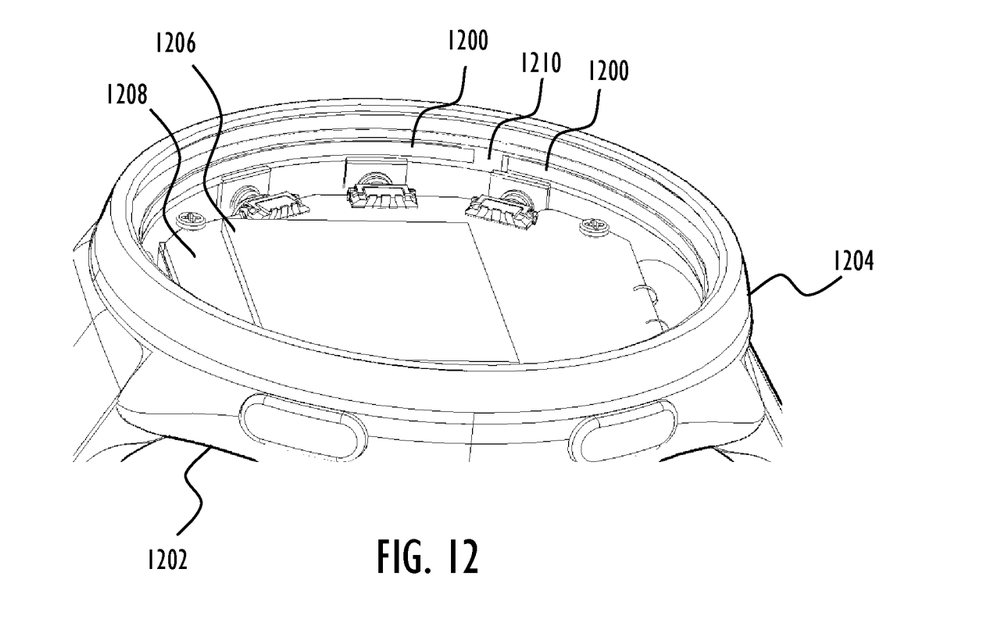
FIGS. 12 and 13 illustrate a folded dipole antenna and a wrist-worn training computer.
Figure 13:
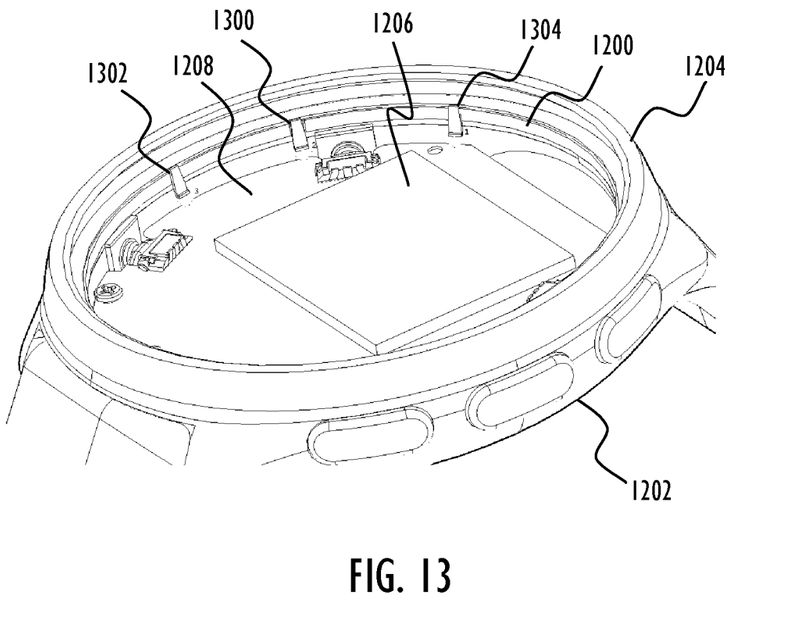

The position of the folded dipole antenna, or the first part of the antenna, within the wrist device is illustrated in more detail in FIGS. 12 and 13. A conductive element 1200 is embedded in the inner wall of the casing 1202. A bezel 1204 and an electromagnetic shield 1206 are also shown. A feed contact 1300 is between a first ground contact 1302 and a second ground contact 1304. The ground contacts are coupled to a ground plane 1208. A break 1210 between the ends of the conductive element 1200 may be filled by the non-conductive casing extending into the break. The break may be approximately 2 mm wide, i.e. the ends of the conductive element may be separated by a distance of approximately 2 mm.

As wrist devices are often held in the positions illustrated in FIG. 11, or in a position between the two illustrated positions, the radiation pattern of the folded dipole antenna is often directed towards navigational satellites when the wrist device is in use. This is due to the advantageous positioning of the folded dipole antenna within the wrist device and allows for good reception of RHCP signals from navigational satellites.

Figure 14:
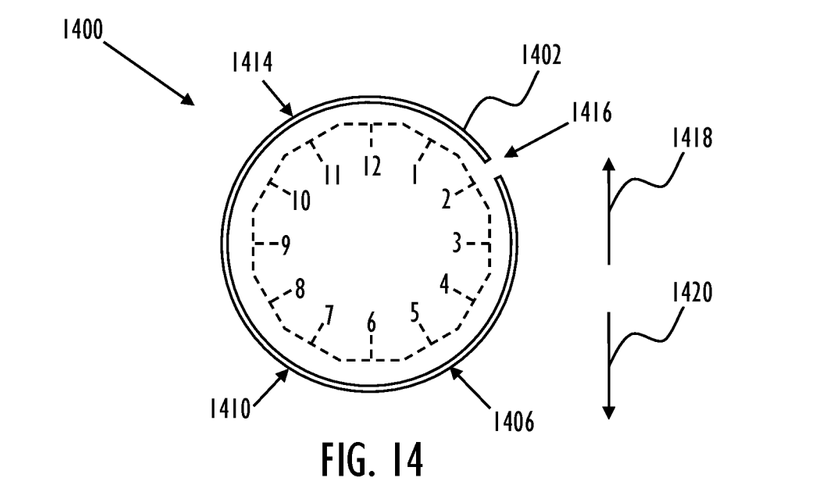
FIG. 14 illustrates a folded dipole antenna and an imaginary clock face.

FIG. 14 illustrates alternative embodiments of the folded dipole antenna 1400 wherein the conductive element 1402 is also penannular. In an embodiment, the first ground point 1410 is located $1/6^{th}$ of a full revolution clockwise of the feed point 1406, the second ground point 1414 is located opposite the feed point, and the break 1416 between the ends of the conductive element is located $\frac{1}{4}^{th}$ of a full revolution clockwise of the second ground point.

The folded dipole antenna according to the above embodiment may be configured to receive RHCP signals from navigational satellites. The radiation pattern of the above folded dipole antenna may be focused in multiple directions ranging from an upwards direction 1418, to a perpendicular direction towards the viewer of FIG. 14, and to a downwards direction 1420, for example.

In an embodiment of the wrist-worn training computer, the folded dipole antenna is positioned relative to an imaginary clock face of the wrist-worn training computer so that the break between the open ends of the antenna is in a direction of 2 o'clock, the feed point is in a direction of 5 o'clock, the first ground point is in the direction of 7 o'clock, and the second ground point is in a direction of 11 o'clock. The positioning of the folded dipole antenna with respect to an imaginary clock face is also illustrated in FIG. 14.

The radiation pattern of the folded dipole antenna according to the above embodiment may be focused in multiple directions ranging from the direction of 12 o'clock on the imaginary clock face of the wrist-worn training computer, to a perpendicular direction away from the imaginary clock face, which corresponds to a perpendicular direction away from the display screen of the training computer, and to a direction of 6 o'clock on the imaginary clock face, for example. The radiation pattern may therefore be directed towards navigational satellites in multiple orientations of the wrist device, including the orientations shown in FIG. 11.

Figure 15:
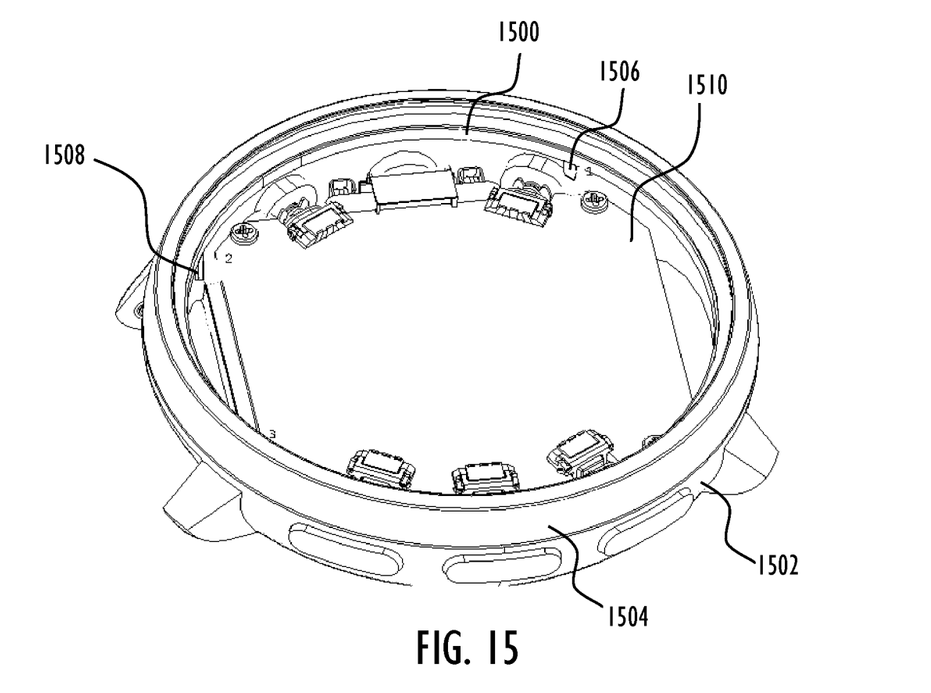
FIGS. 15 and 16 illustrate a folded dipole antenna and a wrist-worn training computer.
Figure 16:
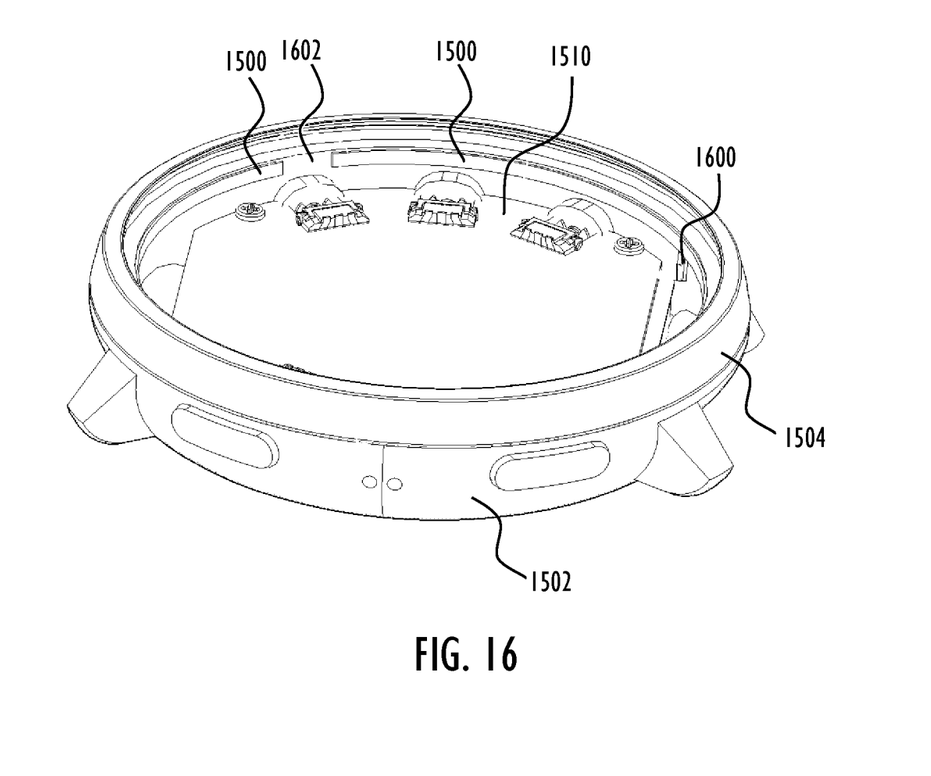

The position of the above folded dipole antenna within the wrist-worn training computer is illustrated in more detail in FIGS. 15 and 16. A conductive element 1500 is embedded in the inner wall of the casing 1502. A bezel 1504 and a feed contact 1600 are also shown. A first ground contact 1506 and a second ground contact 1508 are coupled to a ground plane 1510. A break 1602 between the ends of the conductive element 1500 may be filled by the non-conductive casing extending into the break. The break may be approximately 3.7 mm wide, i.e. the ends of the conductive element may be separated by a distance of approximately 3.7 mm.

Even though the invention has been described with reference to one or more embodiments according to the accompanying drawings, it is clear that the invention is not restricted thereto but can be modified in several ways within the scope of the appended claims. All words and expressions should be interpreted broadly, and they are intended to illustrate, not to restrict, the embodiments. It will be obvious to a person skilled in the art that, as technology advances, the inventive concept can be implemented in various ways.

What is claimed is:

1. A wrist-worn training computer comprising:
   one or more biosensors;
   a casing;
   a display lens having an external surface facing away from the casing, and an internal surface facing towards the casing and positioned against the casing to form an interface between the display lens and the casing, and to enclose together with the casing an enclosed space between the casing and the display lens;
   a first part of an antenna of a satellite navigation receiver disposed within the enclosed space; and
   a gasket positioned along the interface between the internal surface of the display lens and the casing to seal the enclosed space, wherein the gasket comprises electrically conductive material that forms a second part of the antenna, wherein
   the electrically conductive material is an electrically conductive paste comprising electrically conductive particles dispersed in a medium.

2. The wrist-worn training computer of claim 1, wherein the first part of the antenna and the second part of the antenna are capacitively coupled.

3. The wrist-worn training computer of claim 1, wherein the electrically conductive material forms a closed loop.

4. The wrist-worn training computer of claim 3, wherein the electrically conductive material forms an annular loop.

5. The wrist-worn training computer of claim 1, wherein the electrically conductive material forms a penannular shape.

6. The wrist-worn training computer of claim 1, wherein the electrically conductive material extends in a first plane parallel to the display lens and turns to a second plane perpendicular to the display lens.

7. The wrist-worn training computer of claim 1, wherein the gasket comprises a uniform structure comprising the electrically conductive material.

8. The wrist-worn training computer of claim 1, wherein the electrically conductive paste is an electrically conductive adhesive that adheres the display lens to the casing.

9. The wrist-worn training computer of claim 1, wherein the casing is a plastic casing.

10. The wrist-worn training computer of claim 1, wherein the biosensors comprise at least one of: an optical heart rate sensor, an oxygen saturation sensor, a temperature sensor, an electrocardiography sensor, a bioimpedance sensor, a body composition sensor.

* * * * *